US010646415B1

(12) United States Patent
Machover

(10) Patent No.: US 10,646,415 B1
(45) Date of Patent: May 12, 2020

(54) HAIR-COLORING COMPOSITIONS, AEROSOL PRODUCTS, AND METHODS FOR COLORING HAIR

(71) Applicant: L'OREAL, Paris (FR)

(72) Inventor: Sarah Barrie Machover, New York, NY (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/176,064

(22) Filed: Oct. 31, 2018

(51) Int. Cl.
  A61Q 5/10      (2006.01)
  A61K 8/04      (2006.01)
  A61K 8/81      (2006.01)
  A61K 8/49      (2006.01)
  A61K 8/41      (2006.01)
  A61K 8/33      (2006.01)

(52) U.S. Cl.
  CPC .......... *A61K 8/046* (2013.01); *A61K 8/33* (2013.01); *A61K 8/411* (2013.01); *A61K 8/4926* (2013.01); *A61K 8/4946* (2013.01); *A61K 8/8152* (2013.01); *A61K 8/8176* (2013.01); *A61K 8/8182* (2013.01); *A61Q 5/10* (2013.01); *A61K 2800/4324* (2013.01); *A61K 2800/594* (2013.01); *A61K 2800/87* (2013.01)

(58) Field of Classification Search
  CPC ........ A61Q 5/10; A61Q 5/065; A61K 8/4926; A61K 8/418; A61K 8/49; A61K 8/8152; A61K 2800/432; A61K 8/34; A61K 8/817; A61K 8/8158; A61K 8/8182; A61K 8/4913; A61K 8/73; A61K 8/8164; A61K 8/8129; A61K 2800/48; A61K 8/8176; A61K 8/8135
  See application file for complete search history.

(56) References Cited

U.S. PATENT DOCUMENTS

| 4,820,308 | A  | 4/1989  | Madrange et al. |
| 4,979,961 | A  | 12/1990 | Junino et al. |
| 5,008,105 | A  | 4/1991  | Grollier et al. |
| 5,137,538 | A  | 8/1992  | Madrange et al. |
| 5,158,762 | A  | 10/1992 | Pierce |
| 5,344,464 | A  | 9/1994  | Madrange et al. |
| 5,505,741 | A  | 4/1996  | Junio et al. |
| 5,534,036 | A  | 7/1996  | Junino et al. |
| 5,542,952 | A  | 8/1996  | Genet et al. |
| 5,609,649 | A  | 3/1997  | Junino et al. |
| 6,090,160 | A  | 7/2000  | Junino et al. |
| 6,136,042 | A  | 10/2000 | Maubru |
| 6,187,057 | B1 | 2/2001  | Maubru |
| 6,824,764 | B2 | 11/2004 | Devin-Baudoin et al. |
| 6,824,765 | B2 | 11/2004 | Gawtrey et al. |
| 7,208,019 | B2 | 4/2007  | Lalleman et al. |
| 7,713,310 | B2 | 5/2010  | Lalleman |
| 2003/0121109 | A1 | 7/2003 | Devin-Baudoin et al. |
| 2004/0010863 | A1 | 1/2004 | Gawtrey et al. |
| 2005/0058608 | A1 | 3/2005 | Rollat-Corvol et al. |
| 2005/0058676 | A1 | 3/2005 | Rollat-Corvol et al. |
| 2005/0144739 | A1 | 7/2005 | Lalleman et al. |
| 2006/0105003 | A9 | 5/2006 | Rollat-Corvol et al. |
| 2006/0182697 | A1 | 8/2006 | Lalleman et al. |
| 2007/0251026 | A1 | 11/2007 | Lalleman et al. |
| 2008/0134449 | A1 | 6/2008 | Lalleman |
| 2008/0145327 | A1 | 6/2008 | Cajan et al. |
| 2008/0152610 | A1 | 6/2008 | Cajan et al. |
| 2010/0017971 | A1 | 1/2010 | Chiba et al. |
| 2010/0021396 | A1* | 1/2010 | Kleen .................... A61K 8/046 424/47 |
| 2010/0047201 | A1 | 2/2010 | Lalleman et al. |
| 2010/0147319 | A1 | 6/2010 | Lalleman |
| 2010/0147320 | A1 | 6/2010 | Lalleman |
| 2011/0186071 | A1 | 8/2011 | Miyabe et al. |
| 2011/0214682 | A1 | 9/2011 | Fujinuma et al. |
| 2012/0132226 | A1 | 5/2012 | Wood et al. |
| 2012/0244083 | A1 | 9/2012 | Schmid et al. |
| 2013/0081647 | A1 | 4/2013 | Vohra et al. |
| 2016/0038398 | A1 | 2/2016 | Cajan et al. |
| 2017/0224605 | A1* | 8/2017 | Goutsis .................. A61K 8/365 |
| 2017/0239152 | A1 | 8/2017 | Goutsis |

FOREIGN PATENT DOCUMENTS

CN          102423284 A       4/2012

OTHER PUBLICATIONS

"L'Oreal Studio Line Hot & Go Hairspray," https://www.google.com/search?source=hp&ei=qMTZW7HwF4qG5wK68JqoCQ&q=L%27Oreal+Studio+Line+Hot'%26+Go+Hairspary&btnK=Google+Search&oq=L%27Oreal+Studio+Line+Hot+%26+Go+Hairspary&gs_l=psy-ab.3..33i22i29i30j33i10.3055.16295..16633...0.0..0.92.2133.38......0....1..gws-.
"Brite Organix Liquid Hair Chalk," https://www.forever21.com/us/shop/catalog/product/f21/acc_beauty-hair-styling-product/1000106246.
"Models Own Festival Collection Colour Hair Spray," https://www.asos.com/models-own/models-own-coloured-hairspray/prd/5311306.
"Colorsmash Color Kisses Hairspray," https://www.houseofbeautyworld.com/cocokiha15oz.html?cmp=googleproducts&kw=cocokiha15oz&gclid=EAIaIQobChMItce-vfyw3gIVFFuGCh1FZg90EAQYASABEgLwO_D_BwE.

(Continued)

*Primary Examiner* — Eisa B Elhilo
(74) *Attorney, Agent, or Firm* — Polsinelli PC

(57) ABSTRACT

The present disclosure relates to hair-coloring compositions comprising direct dyes, and aerosol hair-coloring products comprising the hair-coloring compositions. The hair-coloring compositions include: (a) at least one direct dye selected from nitro-phenylenediamines, nitro-aminophenols, azo dyes, anthraquinones, triarylmethane dyes, indophenols, and a mixture thereof; (b) at least one nonionic film forming polymer; (c) at least one thickening agent; (d) at least 40 wt. % of water, based on the total weight of the compositions; and (e) 40 wt. % or less of ethanol, based on the total weight of the composition. The hair-coloring compositions can be combined with a propellant and incorporated into a canister to provide a hair-coloring aerosol product. The compositions and aerosol products are useful for coloring hair.

20 Claims, No Drawings

(56) References Cited

OTHER PUBLICATIONS

"Michel Mercier SOS Color Recover," https://www.amazon.com/stores/Michel+Mercier/SOS+Color+Recover/page/4B5D1B2A-8635-4DCF-B4B7-6AF10BBD958E.

"Schwarzkopf BlondMe Toning Spray," https://www.amazon.com/Schwarzkopf-Professional-BlondMe-Enhancing-Conditioner/dp/B01MRA974K.

* cited by examiner

HAIR-COLORING COMPOSITIONS, AEROSOL PRODUCTS, AND METHODS FOR COLORING HAIR

FIELD OF THE DISCLOSURE

The present disclosure relates to water-based direct dye compositions that quickly and effectively color hair; and to methods for coloring hair.

BACKGROUND

There are many methods and products available for changing the natural color of hair. Semi-permanent or temporary dyeing methods, or direct dyeing methods, temporarily change the color of hair. These methods can change the color of the hair to varying degrees and the color change may withstand several rounds of shampooing. Many consumers seek more permanent results, and therefore default to oxidative dye products that contain hydrogen peroxide or other oxidants. In order to provide the consumer with the shade, longevity, and the intensity of color desired, an oxidative coloring process is utilized. Permanent hair dyeing formulations typically include primary intermediates (also known as oxidative hair dye precursors or developers) and couplers (also known as color modifiers or secondary intermediates). These dye precursors are sufficiently small, polar and soluble to diffuse into the hair shaft where, once activated by an oxidizing agent under basic conditions, such as hydrogen peroxide, the primary intermediates react with other dye precursors, e.g., couplers, to form larger colored chromophores in the hair shaft. The chromophores formed in the hair shaft do not readily diffuse from the hair during subsequent washing.

The oxidative coloring of hair can require long processing times. For instance, oxidative coloring processes involve premixing a coloring base and a developer. This mixture is then applied to the hair and must remain on the hair for a long period of time (an extended "processing" time) to potentiate the desired color change. Direct dyes, however, do not require admixing and activation by oxidizing agents and do not require long processing times.

Many attempts have been made by the hair color industry to enhance the washfastness (tenacity) of direct dyes by either forming a covalent bond between chromophore and proteins inside hair or increasing the number of binding sites, typically cationic centers, on the chromophore. However, each attempt has its drawbacks. The approach through covalent bonding does not differentiate proteins in hair from skin. The approach through multiple binding sites on the dyes (i.e. multiple positive charges to interact with negative sites on hair, either by bonding several monocationic dyes together or by installing multiple cationic centers on a single chromophore) runs into the obstacles of uneven color due to uneven damage (negative charges) along the length of the hair fibers and reduced dye penetration into hair fibers because the dyes are typically at least twice as large as common oxidative dye precursors. An increase in the number of binding sites minimizes bleeding and color loss caused by rinsing by providing stronger hair-chromophore interactions. However, the same strong binding force to the cuticle also prevents the chromophores from penetrating deep into the cortex of hair, because it is difficult for dyes with multiple positive charges to diffuse through negatively charged networks of keratin proteins. Additionally, since polycationic dyes remain bound to the hair surface rather than penetrating into the fiber, it is difficult to produce dark shades, due to limited binding sites on the surface of hair.

Furthermore, the dying processes using direct dyes typically involve application of creams containing the direct dyes to the hair. These creams must be massaged with the hands or combed-into the hair to provide uniform coverage. This process can be messy and time consuming. Improving the washfastness (tenacity) of direct dye products and simplifying the coloring process is desirable to both consumers and to professional hair stylist.

SUMMARY OF THE DISCLOSURE

The present disclosure relates to hair coloring compositions comprising direct dyes, in particular, hair-coloring compositions (useful as juice) for use in hair-coloring aerosol spray products. The coloring compositions and the aerosol spray products are useful in methods for coloring hair, especially human hair. The coloring compositions, products, and methods provide excellent color deposition and intensity to hair and the color exhibits surprising tenacity (withstands multiple washings without appreciable fading). The inventors discovered that contrary to conventional wisdom, limiting the amount of ethanol in favor of higher amounts of water resulted in a surprising improvement in the color deposition and tenacity of direct dyes. The coloring is accomplished without requiring harsh oxidative chemical processing. The hair-coloring aerosol spray products are easy to use, color hair quickly, and are surprisingly effective.

The hair coloring compositions typically include:
  (a) at least one direct dye, for example, selected from nitro-phenylenediamines, nitro-aminophenols, azo dyes, anthraquinones, triarylmethane dyes, indophenols, and a mixture thereof;
  (b) at least one nonionic film forming polymer;
  (c) at least one thickening agent;
  (d) at least 40 wt. % of water, based on the total weight of the composition; and
  (e) 40 wt. % or less of ethanol, based on the total weight of the composition.

As indicated above, the amount by weight of water is the same or higher than the amount by weight of ethanol. More specifically, the weight ratio of water to ethanol (water: ethanol) is about 1:1 to about 5:1. Additionally, the total amount of volatile organic compounds (VOC) in the compositions is typically less than 55 wt. %.

The coloring compositions may be used in methods for coloring hair. Such methods include, for example: (i) applying the coloring composition to the hair; (ii) allowing the coloring composition to remain on the hair for a period of time, for example, from about 5 minutes to about 30 minutes; and (iii) rinsing the coloring composition from the hair.

The hair-coloring compositions are particularly useful in aerosol-spray products. Therefore, the disclosure further relates to aerosol hair-coloring products comprising a container/canister, the container/canister comprising:
  a vapor phase comprising a propellant; and
  a hair coloring juice phase comprising:
    (a) at least one direct dye selected from nitro-phenylenediamines, nitro-aminophenols, azo dyes, anthraquinones, triarylmethane dyes, indophenols, and a mixture thereof;
    (b) at least one nonionic film forming polymer;
    (c) at least one thickening agent;
    (d) at least 40 wt. % of water, based on the total weight of the juice phase; and (e) 40 wt. % or less of ethanol, based on the total weight of the juice phase.

The amount by weight of water in the juice phase is the same or higher than the amount by weight of ethanol in the juice phase, for example, the weight ratio of water to ethanol (water:ethanol) may be about 1:1 to about 5:1. Additionally, the total amount of volatile organic compounds (VOC) in the product is typically less than 55 wt. %.

The aerosol spray products may be used in methods for coloring hair. Such methods include, for example: dispensing (e.g., spraying) the hair coloring juice phase from the hair coloring product onto hair; (ii) allowing the hair coloring juice phase to remain on the hair for about 5 to about 30 minutes; and (iii) rinsing the hair coloring juice phase from the hair.

DETAILED DESCRIPTION OF THE DISCLOSURE

The hair-coloring compositions of the instant disclosure typically include:
(a) about 0.01 to about 15 wt. % of at least one direct dye selected from nitro-phenylenediamines, nitro-aminophenols, azo dyes, anthraquinones, triarylmethane dyes, indophenols, and a mixture thereof;
(b) about 0.1 to about 25 wt. % of at least one nonionic film forming polymer;
(c) about 0.1 to about 10 wt. % of at least one thickening agent;
(d) at least 40 wt. % of water; and
(e) 40 wt. % or less of ethanol;
wherein the weight ratio of water to ethanol (water:ethanol) is about 1:1 to about 5:1; the total amount of volatile organic compounds (VOC) is less than 55 wt. %; and all percentages by weight are based on the total weight of the hair coloring composition.

The hair-coloring compositions may include (or exclude) additional components, for example, silicones, water-soluble solvents, fillers, salts (e.g., sodium chloride), surfactants, pH adjusting agents, buffering agents, preservatives, fragrances, etc. The hair-coloring compositions are non-oxidative compositions and are therefore typically free or essentially free of oxidative dye precursors. Furthermore, the hair-coloring compositions can be free or essentially free of pigments. Non-limiting examples of pigments (which may optionally be included or excluded) include silicon powder, mica, titanium dioxide, iron oxide, bismuth oxychloride, diatomaceous earth, and aluminum-clad epoxy resin.

Both direct dyes and pigments are used to color hair but they differ in that pigments are finely ground color particles dispersed through a carrying base (e.g., a coloring composition) and take effect by being spread over the surface (e.g., hair). Direct dyes, also called substantive dyes, are a class of colored compounds that are typically water-soluble and have an affinity for fibers such as hair. Direct dyes can be applied to fibers, such as hair, without the use of a mordent and are often azo and nitro compounds. In some instances, the only hair coloring compounds in the hair-coloring compositions are direct dyes, for example, direct dyes selected from nitro-phenylenediamines, nitro-aminophenols, azo dyes, anthraquinones, triarylmethane dyes, indophenols, and a mixture thereof. A more exhaustive but non-limiting list of useful direct dyes is included under the heading, "Direct Dyes."

Volatile organic compounds (VOCs) are organic chemicals that have a high vapor pressure at ordinary room temperature (25° C.). Their high vapor pressure results from a low boiling point, which causes large numbers of molecules to evaporate or sublimate from the liquid or solid form of the compound and enter the surrounding air, a trait known as volatility. The term is well understood in the art. For purposes of the instant disclosure, the term is defined in the same manner as the US Environmental Protection Agency (EPA) as of 2018 (see, e.g., epa.gov/indoor-air-quality-iaq/technical-overview-volatile-organic-compounds). Non-limiting examples of VOCs in the aerosol products of the instant disclosure include propellant (e.g., dimethyl ether) and ethanol.

As noted above, the hair coloring compositions typically include 55 wt. % or less of VOCs, based on the total weight of the hair coloring composition. In some instances, the hair-coloring compositions include 50 wt. % or less of VOCs, 45 wt. % or less of VOCs, 40 wt. % or less of VOCs, 35 wt. % or less of VOCs, 30 wt. % or less of VOCs, 25 wt. % or less of VOCs, or 20 wt. % or less of VOCs. In some instances, the only VOC in the hair-coloring composition is ethanol.

The hair-coloring compositions typically include at least 40 wt. % of water, based on the total weight of the hair-coloring composition. In some instances, the hair-coloring compositions include at least 50 wt %, at least 60 wt. %, at least 65 wt. %, or at least 70 wt. % of water. The total amount of water may be at least 40 to about 90 wt. %, at least 50 to about 90 wt. %, at least 60 to about 90 wt. %, at least 65 to about 90 wt. %, at least 70 to about 90 wt. %, at least 40 to about 80 wt. %, at least 50 to about 80 wt. %, at least 60 to about 80 wt. %, at least 65 to about 80 wt. %, or at least 70 to about 80 wt. %, based on the total weight of the hair-coloring composition.

The hair-coloring compositions typically include 40 wt. % or less of ethanol, based on the total weight of the hair-coloring composition. In some instances, the hair-coloring compositions include 35 wt. % or less, 30 wt. %, or less, 28 wt. % or less, 26 wt. % or less, or 25 wt. % or less of ethanol. The total amount of ethanol may be from about 5 to 40 wt. %, about 5 to 35 wt. %, about 5 to 30 wt. %, about 5 to 28 wt. %, about 5 to 26 wt. %, or about 5 to 25 wt. %, based on the total weight of the hair-coloring compositions.

The amount of water in the hair-coloring compositions is typically equal or higher than the amount of ethanol; and may be equal or higher than the total amount of VOCs in the hair-coloring composition. For example, the ratio of water to ethanol (water:ethanol) may be from about 1:1 to about 5:1, about 1:1 to about 4:1, about 1:1 to about 3:1, about 2:1 to about 5:1, or about 2:1 to about 4:1. Similarly, the ratio of water to total VOCs (water:VOCs) may be from about 1:1 to about 5:1, about 1:1 to about 4:1, about 1:1 to about 3:1, about 2:1 to about 5:1, or about 2:1 to about 4:1.

The hair-coloring compositions include at least one nonionic film forming polymer. Many aerosol products (e.g., hair spray, etc.) include anionic film-forming polymer. The hair-coloring compositions of the instant case may optionally include anionic film-forming polymers but they are not required and in some instances are preferably excluded from the compositions. With respect to nonionic film forming polymers, non-limiting examples include:
polyalkyloxazolines;
vinyl acetate homopolymers;
vinyl acetate copolymers;
homopolymers and copolymers of acrylic esters;
copolymers of acrylonitrile and a nonionic monomer;
styrene homopolymers;

styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine);

polyamides;

vinylpyrrolidone homopolymers;

copolymer of vinylpyrrolidone and vinyl acetate monomers;

vinyllactam homopolymers including and polyvinylcaprolactam; and vinyllactam copolymers, such as poly(vinylpyrrolidone/vinyllactam) copolymer, poly(vinylpyrrolidone/vinyl acetate) copolymers;

poly(vinylpyrrolidone/vinyl acetate/vinyl propionate) terpolymers; and a mixture thereof.

In some instances, the hair-coloring compositions preferably include at least one nonionic film forming polymer selected from VP/VA copolymer (or PVP/VA copolymer), PVP, or a mixture thereof. A more exhaustive but non-limiting list of useful nonionic film polymers is included under the heading "Nonionic Film Forming Polymers."

Thickening agents (also referred to as thickeners or viscosity modifying agents) are well known. Thickening agents may be nonionic, anionic, or cationic. The thickening agents most useful in the hair-coloring compositions of the instant case are anionic and/or nonionic. A more exhaustive but non-limiting list of useful thickening agents is included under the heading, "Thickening Agents."

Methods for coloring hair with the hair-coloring compositions include applying the hair-coloring composition to the hair. The hair-coloring compositions may be allowed to remain on the hair for a period of time to allow for the direct dyes to penetrate/attach to the hair. After a period of time, the hair-coloring compositions may be rinsed from the hair. After rinsing, the hair may optionally be shampooed and/or styled. The amount of time that the hair-coloring compositions is allowed to remain on the hair before rinsing (i.e., the total processing time) may vary. The hair-coloring composition may be allowed to remain on the hair for about 5 to about 45 minutes, for about 5 to about 40 minutes, for about 5 to about 30 minutes, for about 10 to about 45 minutes, for about 10 to about 40 minutes, for about 10 to about 30 minutes, or about 15 to about 25 minutes.

The hair-coloring compositions can be applied to all of the hair of the head or may be applied to select portions of the hair of the head. The term "hair of the head" relates to the hair on the top of a head and does not include the hair of eyelashes and eyebrows. Nonetheless, the methods of the instant disclosure can be used to color eyelashes and/or eyebrows if such coloring is desired. Application to select portions or sections (chunks) of hair can be used to provide a highlighting effect. The hair-coloring compositions can be applied to dry hair or to wet or damp hair. For instance, the hair may be shampooed or rinsed prior to the application of a hair-coloring composition, for example, to ensure that hair styling products and/or contamination is removed from the hair prior to coloring the hair.

The hair-coloring compositions described throughout this disclosure are particularly useful in aerosol-spray products. Therefore, the disclosure further relates to aerosol hair-coloring products. Such products typically include a canister (or a container) that comprises a vapor phase comprising a propellant and a hair coloring juice phase. The hair-coloring compositions described throughout the instant disclosure are particularly well suited to serve as the juice phase. Therefore, throughout the disclosure, the "hair-coloring compositions" and the "hair-coloring juice phase" can be interchangeable. In other words, any components, characteristics, or amounts described for the hair-coloring compositions equally applies to the hair-coloring juice phase (and vice versa).

The aerosol hair-coloring products typically include a container/canister, the container/canister comprising:

a vapor phase comprising a propellant; and a hair-coloring juice phase comprising:

(a) at least one direct dye selected from nitro-phenylenediamines, nitro-aminophenols, azo dyes, anthraquinones, triarylmethane dyes, indophenols, and a mixture thereof;

(b) at least one nonionic film forming polymer;

(c) at least one thickening agent;

(d) at least 40 wt. % of water, based on the total weight of the juice phase; and (e) 40 wt. % or less of ethanol, based on the total weight of the juice phase.

The amount by weight of water in the juice phase is the same or higher than the amount by weight of ethanol in the juice phase, for example, the weight ratio of water to ethanol (water:ethanol) may be about 1:1 to about 5:1. Additionally, the total amount of volatile organic compounds (VOC) in the product is typically less than 55 wt. %.

The aerosol hair-coloring products, in particular the juice phase, may include (or exclude) additional components, for example, silicones, water-soluble solvents, fillers, salts (e.g., sodium chloride), surfactants, pH adjusting agents, buffering agents, preservatives, fragrances, etc. The aerosol hair-coloring products are non-oxidative products and are therefore are typically free or essentially free of oxidative dye precursors. Furthermore, the aerosol hair-coloring products can be free or essentially free of pigments. Non-limiting examples of pigments (which may optionally be included or excluded) include silicon powder, mica, titanium dioxide, iron oxide, bismuth oxychloride, diatomaceous earth, and aluminum-clad epoxy resin.

In some instances, the only hair coloring compounds in the aerosol hair-coloring products are direct dyes, for example, direct dyes selected from nitro-phenylenediamines, nitro-aminophenols, azo dyes, anthraquinones, triarylmethane dyes, indophenols, and a mixture thereof. A more exhaustive but non-limiting list of useful direct dyes is included under the heading, "Direct Dyes."

The aerosol hair-coloring products typically include 70 wt. % or less of VOCs, based on the total weight of the hair-coloring composition (juice) and propellant (i.e., the total weight of the content inside of a container or canister that houses the hair-coloring juice phase and the propellant(s)). In some instances, the hair-coloring products include 66 wt. % or less of VOCs, 60 wt. % or less of VOCs, 55 wt. % or less of VOCs, or 50 wt. % or less based on the total weight of the hair-coloring composition (juice) and propellant (i.e., the total weight of the content inside of a container or canister that houses the hair-coloring juice phase and the propellant(s)). In some instances, the only VOCs in the hair-coloring product are the ethanol and the propellant.

The hair-coloring juice typically include at least 40 wt. % of water, based on the total weight of the hair-coloring juice. In some instances, the hair-coloring juice includes at least 50 wt %, at least 60 wt. %, at least 65 wt. %, or at least 70 wt. % of water. The total amount of water may be at least 40 to about 90 wt. %, at least 50 to about 90 wt. %, at least 60 to about 90 wt. %, at least 65 to about 90 wt. %, at least 70 to about 90 wt. %, at least 40 to about 80 wt. %, at least 50 to about 80 wt. %, at least 60 to about 80 wt. %, at least 65 to about 80 wt. %, or at least 70 to about 80 wt. %, based on the total weight of the hair-coloring juice.

The hair-coloring juice typically includes 40 wt. % or less of ethanol, based on the total weight of the hair-coloring composition. In some instances, the hair-coloring juice includes 35 wt. % or less, 30 wt. %, or less, 28 wt. % or less, 26 wt. % or less, or 25 wt. % or less of ethanol. The total amount of ethanol may be from about 5 to 40 wt. %, about 5 to 35 wt. %, about 5 to 30 wt. %, about 5 to 28 wt. %, about 5 to 26 wt. %, or about 5 to 25 wt. %, based on the total weight of the hair-coloring juice.

The amount of water in the hair-coloring juice is typically equal or higher than the amount of ethanol; and may be equal or higher than the total amount of VOCs in the hair-coloring composition. For example, the ratio of water to ethanol (water:ethanol) may be from about 1:1 to about 5:1, about 1:1 to about 4:1, about 1:1 to about 3:1, about 2:1 to about 5:1, or about 2:1 to about 4:1. Similarly, the ratio of water to total VOCs (water:VOCs) may be from about 1:1 to about 5:1, about 1:1 to about 4:1, about 1:1 to about 3:1, about 2:1 to about 5:1, or about 2:1 to about 4:1.

The hair hair-coloring juice typically includes at least one nonionic film forming polymer. Many aerosol products (e.g., hair spray, etc.) include anionic film-forming polymer. The hair-coloring compositions of the instant case may optionally include anionic film-forming polymers but they are not required and in some instances are preferably excluded from the compositions. With respect to nonionic film forming polymers, non-limiting examples include:

- polyalkyloxazolines;
- vinyl acetate homopolymers;
- vinyl acetate copolymers;
- homopolymers and copolymers of acrylic esters;
- copolymers of acrylonitrile and a nonionic monomer;
- styrene homopolymers;
- styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine);
- polyamides;
- vinylpyrrolidone homopolymers;
- copolymer of vinylpyrrolidone and vinyl acetate monomers;
- vinyllactam homopolymers including and polyvinylcaprolactam; and
- vinyllactam copolymers, such as poly(vinylpyrrolidone/vinyllactam) copolymer, poly(vinylpyrrolidone/vinyl acetate) copolymers;
- poly(vinylpyrrolidone/vinyl acetate/vinyl propionate) terpolymers; and a mixture thereof.

In some instances, the hair-coloring juice preferably includes at least one nonionic film forming polymer selected from VP/VA copolymer (or PVP/VA copolymer), PVP, or a mixture thereof. A more exhaustive but non-limiting list of useful nonionic film polymers is included under the heading "Nonionic Film Forming Polymers."

Thickening agents (also referred to as thickeners or viscosity modifying agents) are well known. Thickening agents may be nonionic, anionic, or cationic. The thickening agents most useful in the hair-coloring compositions of the instant case are anionic and nonionic, preferably anionic. A more exhaustive but non-limiting list of useful thickening agents is included under the heading, "Thickening Agents."

The canister or container of aerosol hair-coloring products typically have a spray button or other type of dispensing device that allows a user to dispense material from within the canister or container, including propellant and/or hair-coloring juice. Propellants are known and various types may be used. Non-limiting examples of propellants include dimethyl ether, lower alkanes, such as n-butane, isobutene and propane, fluorohydrocarbons, such as F 152a (1,1-difluorethane) or F 134 (tetrafluorethane). In some cases, particularly useful propellants include dimethyl ether, hydrofluorocarbon 152A, isobutane, propane, butane, and a mixture thereof. Dimethyl ether is a particularly useful and preferred propellant.

Various aerosol devices may be employed. Typically, an aerosol device includes a vessel (e.g., a container or canister) and a dispensing device for dispensing the content of the vessel, such as a spray device. Contained inside the vessel is a vapor phase comprising propellant(s) and a hair-coloring juice phase (liquid phase) comprising the hair-coloring compositions described throughout the instant disclosure. The role of the vapor phase (the propellant(s) in particular) is to provide pressure for expelling the juice phase from the vessel. For example, typical aerosol hair spray devices expel the juice phase in the form of a mist of dispersed droplets. The juice phase is primarily comprised of the hair-coloring compositions of the instant disclosure. Small amounts of propellant(s) or other materials from the vapor phase may be present in the juice phase, for example, to the extent that these components may be partially dispersed or solubilized in the juice phase. Likewise, the vapor phase is primarily comprised of propellant(s). Small amounts of juice phase (or components of the juice phase) may be present in the vapor phase to the extent that the juice phase (or components of the juice phase) are dispersed or solubilized in the vapor phase.

The total amount of propellant incorporated into aerosol hair-coloring product may vary. In some cases, however, an aerosol hair-coloring product may include about 10 to about 60 wt. % of propellant, based on the total weight of the hair-coloring composition (juice) and propellant (i.e., the total weight of the content inside of a container or canister that houses the hair-coloring juice phase and the propellant(s))). In some cases, the total amount of propellant may be about 10 to about 50 wt. %, about 10 to about 45 wt. %, about 10 to about 40 wt. %, about 20 to about 60 wt. %, about 20 to about 50 wt. %, about 10 to about 40 wt. %, or about 25 to about 45 wt. %, based on the total weight of the hair-coloring composition (juice) and propellant (i.e., the total weight of the content inside of a container or canister that houses the hair-coloring juice phase and the propellant(s))).

Methods for coloring hair with the aerosol hair-coloring products include dispensing (for example, spraying) the hair-coloring juice from the aerosol hair-coloring product onto hair. The hair-coloring juice may be allowed to remain on the hair for a period of time to allow for the direct dyes to penetrate/attach to the hair. After a period of time, the hair-coloring juice may optionally be rinsed from the hair. After optional rinsing, the hair may optionally be shampooed and/or styled. The amount of time that the hair-coloring juice is allowed to remain on the hair before rinsing (i.e., the total processing time) may vary. The hair-coloring juice may be allowed to remain on the hair for about 5 to about 45 minutes, for about 5 to about 40 minutes, for about 5 to about 30 minutes, for about 10 to about 45 minutes, for about 10 to about 40 minutes, for about 10 to about 30 minutes, or about 15 to about 25 minutes.

The hair-coloring juice can be dispensed to all of the hair of the head or may be dispensed to select portions of the hair of the hair. The term "hair of the head" relates to the hair on the top of a head and does not include the hair of eyelashes and eyebrows. Nonetheless, the methods of the instant disclosure can be used to color eyelashes and/or eyebrows if such coloring is desired. Application to select portions or sections (chunks) of hair can be used to provide a highlighting effect. The hair-coloring compositions can be dispensed to dry hair or to wet or damp hair. For instance, the hair may be shampooed or rinsed prior to the application of the hair-coloring juice, for example, to ensure that hair styling products and/or contamination is removed from the hair prior to coloring the hair.

More exhaustive but non-limiting examples of components that may be used in the compositions, products, and methods of the instant disclosure are provided below.

Direct Dyes

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (Via) and (VI'a) and the diazo cationic dyes (VIIa) below:

| | |
|---|---|
| Het⁺—C(Rᵃ) =N—N(Rᵇ) —Ar, An⁻ | (Va) |
| Het⁺—C(Rᵃ) —N=N(Rᵇ) —Ar, An⁻ | (V'a) |
| Het⁺—N=N—Ar, An⁻ | (VIa) |
| Ar⁺—N=N—Ar", An⁻ | (VI'a) and |
| Het⁺—N=N—Ar' —N=N—Ar, An⁻ | (VIIa) | in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

Rᵃ and Rᵇ, which may be identical or different, represent a hydrogen atom or a group ($C_1$-$C_8$)alkyl, which is optionally substituted, preferentially with a hydroxyl group;

or alternatively the substituent Rᵃ with a substituent of Het⁺ and/or $R_b$ with a substituent of Ar and/or Rᵃ with $R_b$ form, together with the atoms that bear them, a (hetero)cycloalkyl;

particularly, Rᵃ and $R_b$ represent a hydrogen atom or a group ($C_1$-$C_4$)alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

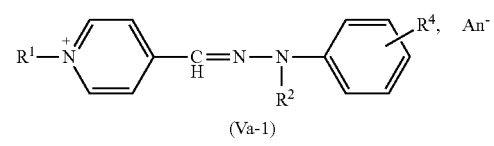

(Va-1)

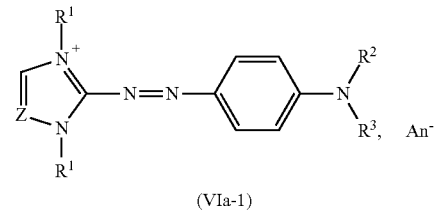

(VIa-1)

formulae (V-1) and (VI-1) with:

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

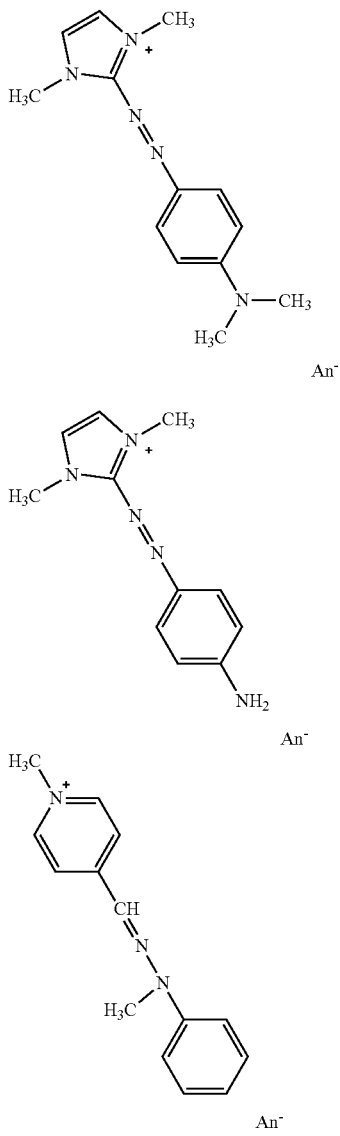

Basic Red 51

Basic Orange 31

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The total amount of direct dyes in the hair-coloring compositions/juice may vary but is typically from about 0.001 to about 10 wt. %, based on the total weight of the hair-coloring composition/juice. In some cases, the total amount of direct dyes in the hair-coloring coloring composition/juice may be from about 0.001 to about 8 wt. %, about 0.001 to about 6 wt. %, about 0.001 to about 5 wt. %, about 0.001 to about 4 wt. %, about 0.001 to about 3 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.1 to about 10 wt. %, about 0.1 to about 8 wt. %, about 0.1 to about 6 wt. %, or about 0.1 to about 5 wt. %, about 0.1 to about 4 wt. %, or about 0.1 to about 3 wt. %, based on the total weight of the aqueous coloring composition/juice.

Nonionic Film Forming Polymers

Nonionic film forming polymers include homopolymers and copolymers derived from at least one nonionic monomer. Nonionic monomers are, for example, acrylamide, methacrylamide, alkyl- and dialkylacrylamide, alkyl- and dialkylmethacrylamide, alkyl acrylate, alkyl methacrylate, vinylcaprolactone, vinylpyrrolidone, vinyl esters, vinyl alcohol, propylene glycol or ethylene glycol, wherein the alkyl groups of these monomers are preferably $C_1$ to $C_7$ alkyl groups and particularly C1 to C3 alkyl groups. Suitable synthetic, nonionic, hair-setting polymers are, for example, the homopolymers of vinylpyrrolidone and the homopolymers of N-vinylformamide. Other suitable synthetic film-forming, nonionic, hair-setting polymers are, for example, the copolymers of vinyl pyrrolidone and vinyl acetate, the terpolymers of vinyl pyrrolidone, vinyl acetate and vinyl propionate, and the polyacrylamides, polyvinyl alcohols or polyethylene glycols with a molecular weight of 800 to 20,000 g/mol.

Nonionic film forming polymers include: polyalkyloxazolines; vinyl acetate homopolymers; vinyl acetate copolymers; homopolymers and copolymers of acrylic esters; copolymers of acrylonitrile and a nonionic monomer; styrene homopolymers; styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine); polyamides; vinylpyrrolidone homopolymers; copolymer of vinylpyrrolidone and vinyl acetate monomers; vinyllactam homopolymers including and polyvinylcaprolactam; and vinyllactam copolymers, such as poly(vinylpyrrolidone/vinyllactam) copolymer, poly(vinylpyrrolidone/vinyl acetate) copolymers; poly(vinylpyrrolidone/vinyl acetate/vinyl propionate) terpolymers; and a mixture thereof.

In some instances, preferred nonionic film forming polymers include copolymer of vinylpyrrolidone and vinyl acetate monomers and/or vinylpyrrolidone homopolymers, for example, VP/VA copolymer (or PVP/VA copolymer), PVP, or a mixture thereof.

The total amount of the nonionic film forming polymers in the hair-coloring compositions/juice can vary but is typically about 0.1 to about 25 wt. %, based on the total weight of the hair-coloring composition/juice. In some instances, the total amount of nonionic film forming polymers is from about 0.1 to about 20 wt. %, about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, about 1 to about 20 wt. %, about 1 to about 15 wt. %, about 1 to about 10 wt. %, or about 1 to about 5 wt. %, based on the total weight of the hair-coloring composition/juice.

Thickening Agents

Thickening agents may be referred to as "thickeners" or "viscosity modifying agents." Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Non-limiting examples of thickening agents include xanthan gum, guar gum, biosaccharide gum, cellulose, acacia Seneca gum, *sclerotium* gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, and acrylamide/sodium acryloyldimethyltaurate copolymer In some instances, the thickening agent(s) are selected from carboxylic acid polymers (e.g., carbomer), crosslinked polyacrylate polymers, polyacrylamide polymers, polysaccharides, gums, and a mixture thereof. A more detailed description of various thickening agents is provided below.

(a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

(b) Crosslinked Polyacrylate Polymers

The compositions of the present disclosure can optionally contain crosslinked polyacrylate polymers useful as thickeners or gelling agents including both cationic and nonionic polymers.

(c) Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

(d) Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

(e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Thickening agents may be nonionic, anionic, or cationic. In some instances, the thickening agents are preferably nonionic or anionic, more preferably, anionic.

Non-limiting examples of nonionic thickening agents include polysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof. In some instances, the hair-coloring compositions/juice preferably include nonionic thickening agent(s).

Non-limiting examples of anionic thickening agents include polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof. In some instances, the hair-coloring compositions/juice preferably include anionic thickening agent(s), in particular, polyacrylate-3.

Non-limiting examples of cationic thickening agents include dimethylaminoethyl methacrylate homopolymers quaternized with methyl chloride or dimethylaminoethyl methacrylate copolymers quaternized with methyl chloride and acrylamide (e.g., methacryloylethyl trimethyl ammonium chloride homopolymer, INCI name: polyquaternium-37). Another suitable example of a cationic thickening agent is a product known by the INCI name of polyacrylate-1 crosspolymer. In some instances, the hair-coloring compositions/juice may preferably exclude cationic thickening agents, i.e., the hair-coloring compositions/juice may be free or essentially free of cationic thickening agents (or cationic thickening polymers).

The total amount of thickening agents in the hair-coloring compositions/juice may vary but is typically about 0.01 to about 10 wt. %, based on the total weight of the hair-coloring composition/juice. In some cases, the total amount of thickening agents may be about 0.01 to about 5 wt. %, about 0.01 to about 3 wt. %, about 0.1 to about 10 wt. %, about 0.1 to about 5 wt. %, or about 0.1 to about 3 wt. %, based on the total weight of the hair-coloring compositions/juice.

Silicone

One or more silicones may optionally be included in the hair-coloring compositions/juice. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. In some cases, dimethicone is preferred silicone.

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

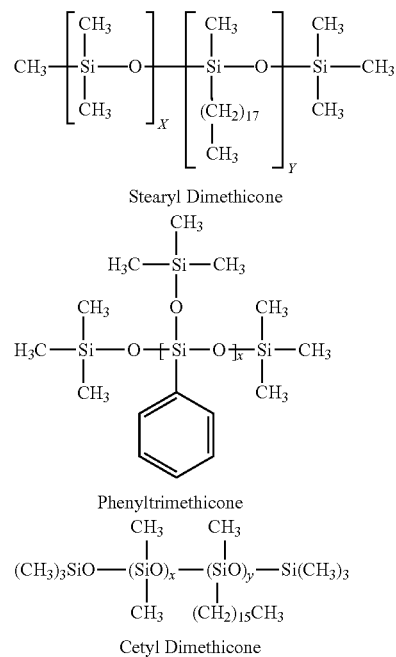

Stearyl Dimethicone

Phenyltrimethicone

Cetyl Dimethicone

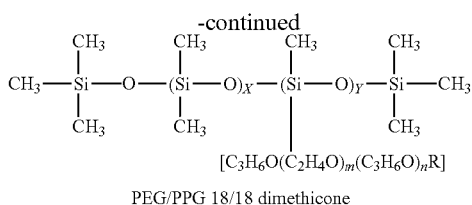

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

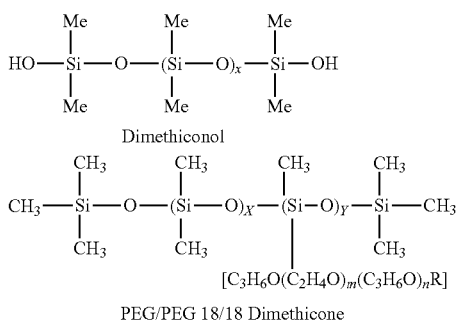

Dimethiconol

PEG/PEG 18/18 Dimethicone

X, y, m, and n are as defined above, and R is a $C_1$ to $C_{10}$ alkyl.

Another type of specific non limiting volatile silicone is a volatile short chain linear alkylmethylsilicone fluid. The volatile short chain linear alkylmethylsilicone fluid has the formula:

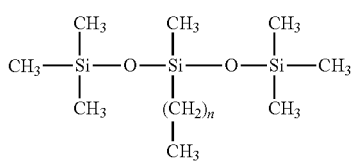

In the above formula, the integer represented by n has a value of five to twelve. Preferably, n has a value of five to eight. Compounds include, for example, 3-hexyl-1,1,1,3,5,5,5-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

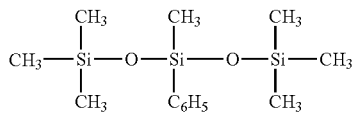

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula [(Me$_2$)SiO]$_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:
a) polysiloxanes corresponding to formula (A):

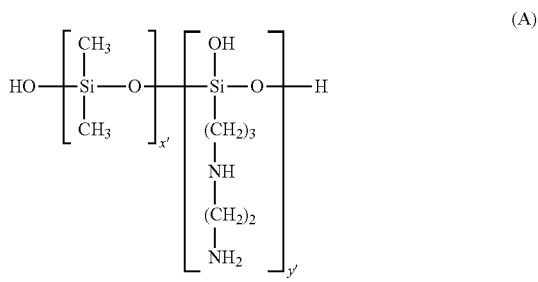

in which x' and y' are integers such that the weight-average molecular weight (Mw) is comprised between about 5000 and 500 000
b) amino silicones corresponding to formula (B):

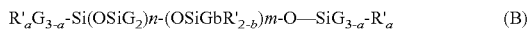

in which:
G, which may be identical or different, designate a hydrogen atom, or a phenyl, OH or $C_1$-$C_8$ alkyl group, for example methyl, or $C_1$-$C_8$ alkoxy, for example methoxy,
a, which may be identical or different, denote the number 0 or an integer from 1 to 3, in particular 0;
b denotes 0 or 1, and in particular 1;
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
R', which may be identical or different, denote a monovalent radical having formula —C$_q$H$_{2q}$L in which q is a number ranging from 2 to 8 and L is an optionally quaternized amino group chosen from the following groups:
—NR"-Q-N(R")$_2$
—N(R")$_2$
—N+(R")$_3$ A-
—N+H(R")$_2$ A-
—N+H$_2$(R") A-
—N(R")-Q-N+R"H$_2$ A-

—NR"-Q-N+(R")$_2$H A-

—NR"-Q-N+(R")$_3$ A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

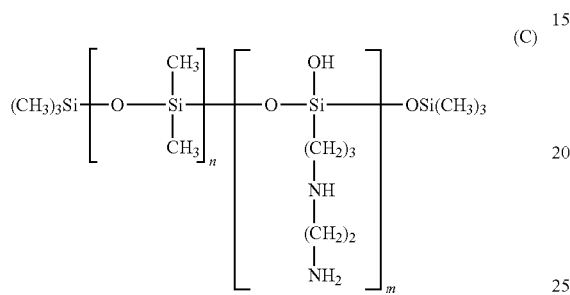

(C)

in which n and m have the meanings given above, in formula B.

Another group of amino silicones corresponding to this definition is represented by silicones having the following formulae (D) or (E):

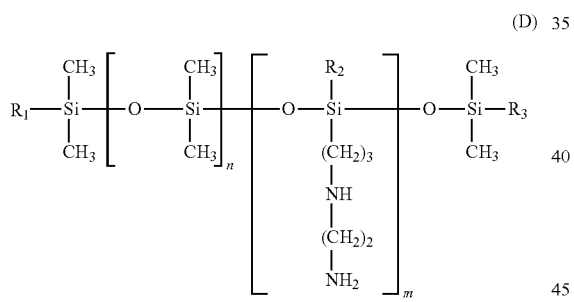

(D)

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

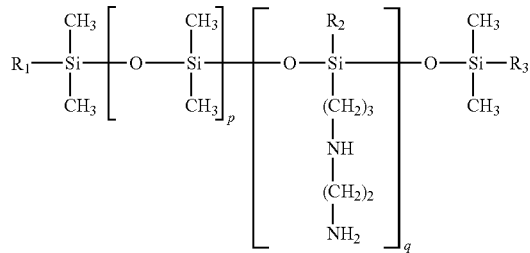

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

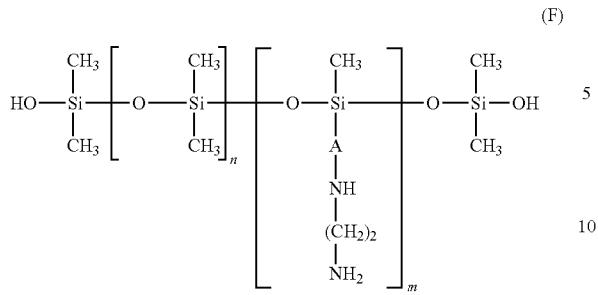

(F)

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

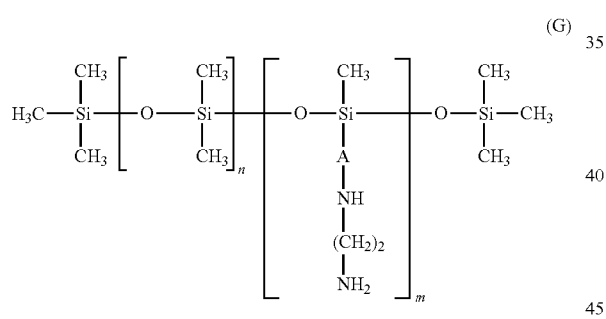

(G)

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

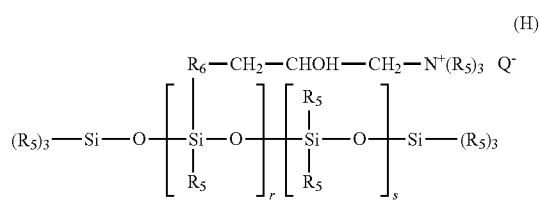

(H)

in which:
$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in patent U.S. Pat. No. 4,185,087.

d) quaternary ammonium silicones having formula (I):

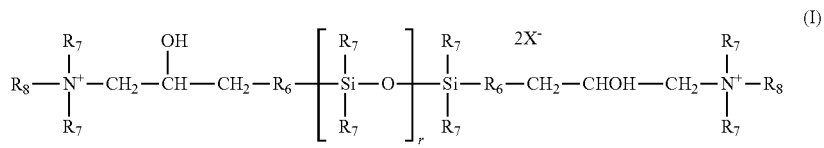

(I)

in which:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

R$_8$, which may be identical or different, represent a hydrogen atom, a monovalent hydrocarbon-based radical containing from 1 to 18 carbon atoms, and in particular a C$_1$-C$_{18}$ alkyl radical, a C$_2$-C$_{18}$ alkenyl radical or a —R$_6$—NHCOR$_7$ radical;

X— is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

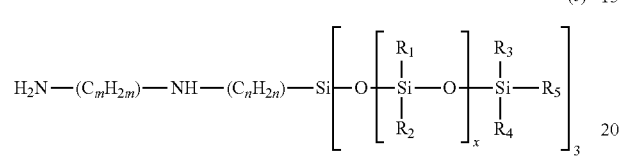

in which:

R$_1$, R$_2$, R$_3$ and R$_4$, which may be identical or different, denote a C$_1$-C$_4$ alkyl radical or a phenyl group;

R$_5$ denotes a C$_1$-C$_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

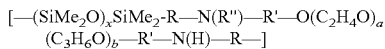

or alternatively

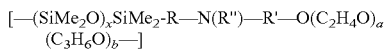

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched C$_2$-C$_{12}$ hydrocarbon-based radical, optionally including one or more heteroatoms such as oxygen; preferably, R denotes an ethylene radical, a linear or branched propylene radical, a linear or branched butylene radical, or a —CH$_2$CH$_2$CH$_2$OCH(OH)CH$_2$— radical; preferentially R denotes a —CH$_2$CH$_2$CH$_2$OCH(OH)CH$_2$— radical;

R', which may be identical or different, represent a divalent linear or branched C$_2$-C$_{12}$ hydrocarbon-based radical, optionally including one or more heteroatoms such as oxygen; preferably, R' denotes an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

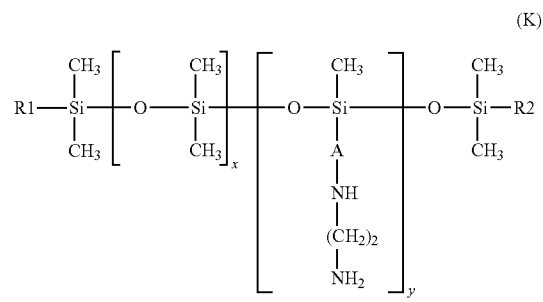

in which:

x and y are numbers ranging from 1 to 5000; preferably, x ranges from 10 to 2000 and especially from 100 to 1000; preferably, y ranges from 1 to 100;

R$_1$ and R$_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —CH$_2$CH$_2$CH$_2$ and —CH$_2$CH(CH$_3$)CH$_2$—.

Preferably, R$_1$ and R$_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, R$_1$ and R$_2$, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: CH$_2$CH$_2$CH$_2$ and —CH$_2$CH(CH$_3$)CH$_2$—; and R$_1$ and R$_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals;

preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Preferably, the amino silicones according to the invention are chosen from the amino silicones of formula (F). A preferred silicone of formula (F) is amodimethicone (INCI name) sold under the tradename XIAMETER® MEM-8299 Cationic Emulsion by Dow Corning.

The total amount of the one or more silicones, if present, may vary but is typically about 0.01 to about 15 wt. %, based on the total weight of the hair-coloring composition/juice. In some cases, the total amount of the one or more silicones is about 0.01 to about 10 wt. %, about 0.01 to about 8 wt. %, about 0.01 to about 5 wt. %, about 0.01 to about 3 wt. %, about 0.1 to about 15 wt. %, about 0.1 to about 10 wt. %, or about 0.1 to about 5 wt. %, or about 0.1 to about 3 wt. %, based on the total weight of the hair-coloring composition/juice.

Water-Soluble Solvents

Non- The term "water-soluble solvent" is interchangeable with the term "water-miscible solvent" and means a compound that at 25° C. and at atmospheric pressure (760 mmHg) has a solubility of at least 50% in water. In some cases, the water-soluble solvent has a solubility of at least 60%, 70%, 80%, or 90% in water at 25° C. and at atmospheric pressure (760 mmHg). Non-limiting examples of water-soluble solvents include, for example, glycerin, alcohols (for example, $C_{1-8}$ or $C_{1-4}$ alcohols), organic solvents, polyols, glycols, and a mixture thereof.

Non-limiting examples of water-soluble solvents include lower monoalcohols and monomeric polyols. Non-limiting examples of lower monoalcohols are those containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

Non-limiting examples of water-soluble organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. In some cases, glycerol is a particularly preferred water soluble solvent.

In some cases, the one or more water-soluble solvents include one or more monomeric polyols. Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the water-soluble solvent(s), if present, in the hair-coloring compositions/juice can vary but is typically about 0.01 to about 20 wt. %, based on the total weight of the hair-coloring composition/juice. In some cases, the total amount of the water-soluble solvent(s) is about 0.01 to about 15 wt. %, about 0.01 to about 10 wt. %, about 0.01 to about 5 wt. %, 0.1 to about 20 wt. %, about 0.1 to about 15 wt. %, about 0.1 to about 10 wt. %, or about 0.1 to about 5 wt. %, based on the total weight of the hair-coloring compositions/juice.

The pH of the hair-coloring compositions/juice can vary greatly, for example, from about 2 to about 12, about 3 to about 11, or about 4 to about 10. In some instances, it may be preferable to have an acidic pH, for example, of about 2 to below 7, about 3 to below 7, about 4 to below 7, about 2 to about 6, about 3 to about 6, or about 4 to about 6.

Surfactants

The hair-coloring compositions/juice may include one or more surfactants, for example, cationic, anionic, nonionic, and/or amphoteric/zwitterionic surfactants. Surfactants are not required but may be useful. In some instances, the hair-coloring compositions/juice may be free or essentially free of surfactants. The hair-coloring compositions/juice may be free or essentially free of anionic surfactants and/or free or essentially free of cationic surfactants and/or free of essentially free of amphoteric/zwitterionic surfactants. The hair-coloring compositions/juice may include as the only type of surfactant, nonionic surfactants. Nonetheless, the hair-coloring compositions/juice may be free or essentially free of nonionic surfactants.

Examples of nonionic surfactants that may be used are described, for example, in the Handbook of Surfactants by M. R. Porter, published by Blackie & Son (Glasgow and London), 1991, pp. 116-178, which is incorporated herein by reference in its entirety. The nonionic surfactant may be alcohols, alpha-diols and ($C_1$-$C_{24}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

The nonionic surfactants are more particularly chosen from monooxyalkylenated or polyoxyalkylenated and monoglycerolated or polyglycerolated nonionic surfactants, and alkyl(poly)glucosides. The oxyalkylene units are more particularly oxyethylene or oxypropylene units, or a combination thereof, preferably oxyethylene units.

Useful nonionic surfactants may include: oxyalkylenated ($C_8$-$C_{24}$)alkylphenols; saturated or unsaturated, linear or branched, oxyalkylenated $C_8$-$C_{40}$ alcohols; saturated or unsaturated, linear or branched, oxyalkylenated $C_8$-$C_{30}$ amides; esters of saturated or unsaturated, linear or branched, $C_8$-$C_{30}$ acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated $C_8$-$C_{40}$ alcohols are useable. In particular, the monoglycerolated or polyglycerolated C $C_8$-$C_{40}$ alcohols correspond to formula (VIII) below:

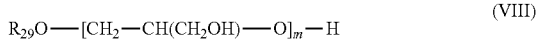

$$R_{29}O\text{---}[CH_2\text{---}CH(CH_2OH)\text{---}O]_m\text{---}H \quad (VIII)$$

in which formula (VIII):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (VIII), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (VIII) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (IX) below:

$$R_{30}O\text{---}(R_{31}O)_t(G)_v \quad (IX)$$

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (IX) that may especially be mentioned are the products sold by the company Cognis under the names Plantaren® (600 CS/U, 1200 and 2000) or Plantacare® (818, 1200 and 2000). Use may also be made of the products sold by the company SEPPIC under the names Triton CG 110 (or Oramix CG 110) and Triton CG 312 (or Oramix® NS 10), the products sold by the company BASF under the name Lutensol GD 70 or the products sold by the company Chem Y under the name AG10 LK. Use may also be made, for example, of the 1,4-($C_8$-$C_{16}$)alkyl-polyglucoside as an aqueous solution at 53% by weight relative to the total weight of the solution, sold by Cognis under the reference Plantacare 818 UP.

The total amount of surfactants in the hair-coloring compositions/juice, if present may be from about 0.01 to about 10 wt. %, based on the total weight of the hair-coloring composition/juice. The total amount of surfactants may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, or about 0.1 to about 3 wt. %, based on the total weight of the hair-coloring compositions/juice.

EMBODIMENTS

In certain embodiments, the instant disclosure relates to a hair coloring composition comprising:

(a) about 0.01 to about 15 wt. %, preferably about 0.05 to about 10 wt. %, more preferably about 0.1 to about 5 wt. % of at least one direct dye selected from nitrophenylenediamines, nitro-aminophenols, azo dyes, anthraquinones, triarylmethane dyes, indophenols, and a mixture thereof;

(b) about 0.1 to about 25 wt. %, preferably about 1 to about 15 wt. %, more preferably about 1 to about 8 wt. % of at least one nonionic film forming polymer for example, film forming polymers selected from polyalkyloxazolines; vinyl acetate homopolymers; vinyl acetate copolymers; homopolymers and copolymers of acrylic esters; copolymers of acrylonitrile and a nonionic monomer; styrene homopolymers; styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine; polyamides; vinylpyrrolidone homopolymers; copolymer of vinylpyrrolidone and vinyl acetate monomers; vinyllactam homopolymers including and polyvinylcaprolactam; and vinyllactam copolymers, such as poly(vinylpyrrolidone/vinyllactam) copolymer, poly(vinylpyrrolidone/vinyl acetate) copolymers; poly(vinylpyrrolidone/vinyl acetate/vinyl propionate) terpolymers; and a mixture thereof, preferably copolymers of vinylpyrrolidone and vinyl acetate monomers and/or vinylpyrrolidone homopolymers, for example, VP/VA copolymer (or PVP/VA copolymer), PVP, or a mixture thereof;

(c) about 0.01 to about 10 wt. %, preferably about 0.05 to about 5 wt. %, more preferably about 0.1 to about 3 wt. % of at least one thickening agent, preferably at least one anionic and/or nonionic thickening polymer, preferably one or more nonionic thickening agents selected from polysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof and/or one or more anionic thickening agents selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof (preferably polyacrylate-3);

(d) at least 40 wt. %, preferably at least 45 wt. % to about 85 wt. %, more preferably at least 50 wt. % or about 80 wt. % of water; and (e) 40 wt. % or less, preferably 35 wt. % or less, more preferably 30 wt. % or less of ethanol;

(f) optionally, about 0.01 to about 15 wt. %, preferably about 0.05 to about 10 wt. %, and more preferably about 0.1 to about 5 wt. % of one or more silicones, for examples, polyorganosiloxanes, polyalkylsiloxanes, polyarylsiloxanes, polyalkarylsiloxanes, polyestersiloxanes, and a mixture thereof, preferably, one or more silicones selected from dimethicone, cyclomethicone, amodimethicone, trimethyl silyl amodimethicone, phenyl trimethicone, trimethyl siloxy silicate, and mixtures thereof;

wherein the weight ratio of water to ethanol (water:ethanol) is about 1:1 to about 5:1, preferably about 2:1 to about 5:1, more preferably about 2:1 to about 4:1;

the total amount of volatile organic compounds (VOC) is less than 55 wt. %, preferably less than 50 wt. %, more preferably less than 45 wt. %; and all percentages by weight are based on the total weight of the hair coloring composition.

In certain embodiments, the instant disclosure relates to an aerosol hair-coloring product comprising a container/canister, the container/canister comprising:

about 10 to about 60 wt. %, preferably about 15 to about 55 wt. %, more preferably about 20 to about 50 wt. % of a vapor phase comprising a propellant, for example, one or more propellants selected from the group consisting of dimethyl ether, propane, n-butane, isobutene, and a mixture thereof (preferably dimethyl ether), wherein the weight percent is based on the total weight of the hair-coloring composition (juice) and propellant (i.e., the total weight of the content inside of a container or canister that houses the hair-coloring juice phase and the propellant(s)); and a hair coloring juice phase comprising:

(a) about 0.01 to about 15 wt. %, preferably about 0.05 to about 10 wt. %, more preferably about 0.1 to about 5 wt. %, based on the total weight of the juice phase, of at least one direct dye selected from nitro-phenylene-diamines, nitro-aminophenols, azo dyes, anthraquinones, triarylmethane dyes, indophenols, and a mixture thereof;

(b) about 0.1 to about 25 wt. %, preferably about 1 to about 15 wt. %, more preferably about 1 to about 8 wt. %, based on the total weight of the juice phase, of at least one nonionic film forming polymer for example, film forming polymers selected from polyalkyloxazolines; vinyl acetate homopolymers; vinyl acetate copolymers; homopolymers and copolymers of acrylic esters; copolymers of acrylonitrile and a nonionic monomer; styrene homopolymers; styrene copolymers (for instance copolymers of styrene and of an alkyl (meth)acrylate; copolymers of styrene, of alkyl methacrylate and of alkyl acrylate; copolymers of styrene and of butadiene; or copolymers of styrene, of butadiene and of vinylpyridine; polyamides; vinylpyrrolidone homopolymers; copolymer of vinylpyrrolidone and vinyl acetate monomers; vinyllactam homopolymers including and polyvinylcaprolactam; and vinyllactam copolymers, such as poly(vinylpyrrolidone/vinyllactam) copolymer, poly(vinylpyrrolidone/vinyl acetate) copolymers; poly(vinylpyrrolidone/vinyl acetate/vinyl propionate) terpolymers; and a mixture thereof, preferably copolymers of vinylpyrrolidone and vinyl acetate monomers and/or vinylpyrrolidone homopolymers, for example, VP/VA copolymer (or PVP/VA copolymer), PVP, or a mixture thereof;

(c) about 0.01 to about 10 wt. %, preferably about 0.05 to about 5 wt. %, more preferably about 0.1 to about 3 wt. %, based on the total weight of the juice phase, of at least one thickening agent, preferably at least one anionic and/or nonionic thickening polymer, preferably one or more nonionic thickening agents selected from polysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof and/or one or more anionic thickening agents selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof (preferably polyacrylate-3);

(d) at least 40 wt. %, preferably at least 45 wt. % to about 85 wt. %, more preferably at least 50 wt. % or about 80 wt. %, based on the total weight of the juice phase, of water; and (e) 40 wt. % or less, preferably 35 wt. % or less, more preferably 30 wt. %, based on the total weight of the juice phase, or less of ethanol;

(f) optionally, about 0.01 to about 15 wt. %, preferably about 0.05 to about 10 wt. %, and more preferably about 0.1 to about 5 wt. %, based on the total weight of the juice phase, of one or more silicones, for examples, polyorganosiloxanes, polyalkylsiloxanes, polyarylsiloxanes, polyalkarylsiloxanes, polyestersiloxanes, and a mixture thereof, preferably, one or more silicones selected from dimethicone, cyclomethicone, amodimethicone, trimethyl silyl amodimethicone, phenyl trimethicone, trimethyl siloxy silicate, and mixtures thereof;

wherein the weight ratio of water to ethanol (water:ethanol) is about 1:1 to about 5:1, preferably about 2:1 to about 5:1, more preferably about 2:1 to about 4:1;

the total amount of volatile organic compounds (VOC) is less than 55 wt. %, preferably less than 50 wt. %, more preferably less than 45 wt. %, based on the total weight of the hair-coloring juice phase.

In certain embodiments, the instant disclosure relates to an aerosol hair-coloring product comprising a container/canister, the container/canister comprising:

about 10 to about 60 wt. %, preferably about 15 to about 55 wt. %, more preferably about 20 to about 50 wt. % of a vapor phase comprising a propellant, for example, one or more propellants selected from the group consisting of dimethyl ether, propane, n-butane, isobutene, and a mixture thereof (preferably dimethyl ether), wherein the weight percent is based on the total weight of the hair-coloring composition (juice) and propellant (i.e., the total weight of the content inside of a container or canister that houses the hair-coloring juice phase and the propellant(s)); and a hair coloring juice phase comprising:

(a) about 0.01 to about 15 wt. %, preferably about 0.05 to about 10 wt. %, more preferably about 0.1 to about 5 wt. %, based on the total weight of the juice phase, of at least one direct dye selected from nitro-phenylenediamines, nitro-aminophenols, azo dyes, anthraquinones, triarylmethane dyes, indophenols, and a mixture thereof;

(b) about 0.1 to about 25 wt. %, preferably about 1 to about 15 wt. %, more preferably about 1 to about 8 wt. %, based on the total weight of the juice phase, of at least one nonionic film forming polymer selected from VP/VA copolymer (or PVP/VA copolymer), PVP, or a mixture thereof;

(c) about 0.01 to about 10 wt. %, preferably about 0.05 to about 5 wt. %, more preferably about 0.1 to about 3 wt. %, based on the total weight of the juice phase, of at least one anionic thickening agents selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof (preferably polyacrylate-3);

(d) at least 40 wt. %, preferably at least 45 wt. % to about 85 wt. %, more preferably at least 50 wt. % or about 80 wt. %, based on the total weight of the juice phase, of water; and (e) 40 wt. % or less, preferably 35 wt. % or less, more preferably 30 wt. %, based on the total weight of the juice phase, or less of ethanol;

(f) optionally, about 0.01 to about 15 wt. %, preferably about 0.05 to about 10 wt. %, and more preferably about 0.1 to about 5 wt. %, based on the total weight of the juice phase, of one or more silicones selected from dimethicone, cyclomethicone, amodimethicone, trimethyl silyl amodimethicone, phenyl trimethicone, trimethyl siloxy silicate, and mixtures thereof;

wherein the weight ratio of water to ethanol (water:ethanol) is about 1:1 to about 5:1, preferably about 2:1 to about 5:1, more preferably about 2:1 to about 4:1;

the total amount of volatile organic compounds (VOC) is less than 55 wt. %, preferably less than 50 wt. %, more preferably less than 45 wt. %, based on the total weight of the hair-coloring juice phase.

Implementation of the present disclosure is provided by way of the following examples. The examples serve to illustrate the technology without being limiting in nature.

Example 1

| | (Inventive Aerosol Hair-Coloring Products) | | |
|---|---|---|---|
| | INCI US | A (wt. %) Red | B (wt. %) Red |
| Direct Dyes | BASIC RED 51 & BASIC YELLOW 87 | <1 | <1 |
| Nonionic Film Former | VP/VA COPOLYMER PVP | 2 | 0.3 |
| Thickening Agent (anionic) | POLYACRYLATE-3 | 0.2 | 0.2 |
| Ethanol | ALCOHOL DENAT. | 16.3 | 16.3 |
| Water | WATER | 45.6 | 47.3 |
| Silicones | DIMETHICONE & BIS-PEG/PPG-14/14 DIMETHICONE | 0.5 | 0.5 |
| Filler | XYLOSE | 0.01 | 0.01 |
| Miscellaneous | SALTS, PH ADJUSTERS, BUFFERING AGENT, PRESERVATIVES, ETC. | <2 | <2 |
| Propellant | DIMETHYL ETHER | 35 | 35 |

Example 2

| | (Influence of Water/Ethanol - Color Uptake) | | | | | | |
|---|---|---|---|---|---|---|---|
| | INCI US | C (wt. %) Red | D (wt. %) Red | E (wt. %) Red | F (wt. %) Magenta | G (wt. %) Magenta | H (wt. %) Magenta |
| Direct Dyes | HC BLUE NO. 15 & BASIC RED 51 | | | | ≤1 | ≤1 | ≤1 |
| | BASIC YELLOW 87 & BASIC RED 51 | ≤1 | ≤1 | ≤1 | | | |
| Nonionic Film Former | VP/VA COPOLYMER | 3 | 3 | 3 | 3 | 3 | 3 |
| Thickening Agent (nonionic) | HYDROXYETHYL-CELLULOSE | 0.5 | 0.5 | 0.5 | 0.5 | 0.5 | 0.5 |
| Ethanol | ALCOHOL DENAT. | 25 | 37.5 | 50 | 25 | 37.5 | 50 |
| Water | WATER | 70 | 58 | 45 | 71 | 58 | 46 |
| Silicone | DIMETHICONE & BIS-PEG/PPG-14/14 DIMETHICONE | 0.8 | 0.8 | 0.8 | 0.8 | 0.8 | 0.8 |
| Filler | XYLOSE | 0.02 | 0.02 | 0.02 | 0.02 | 0.02 | 0.02 |
| Misc. | SALTS, PH ADJUSTERS, BUFFERING AGENT, PRESERVATIVES, ETC. | ≤2 | ≤2 | ≤2 | ≤2 | ≤2 | ≤2 |

Testing was carried out to determine the influence of water and ethanol on color uptake. Compositions C, D, and E are red coloring compositions (juice) that are identical except for the amounts of ethanol and water. Composition C includes 25 wt. % of ethanol (and 70 wt. % of water), Composition D includes 37.% wt. % of ethanol (and 58 wt. % of water), and composition E includes 50 wt. % of ethanol (and 45 wt. % of water). Compositions F, G, and H are magenta coloring compositions (juice) that are also identical except for the amounts of ethanol and water. Composition F includes 25 wt. % of ethanol (and 71 wt. % of water), Composition G includes 37.5 wt. % of ethanol (and 58 wt. % of water), and Composition H includes 50 wt. % of ethanol (and 46 wt. % of water).

About 5 grams of each hair coloring composition (juice) was applied to swatches of yak hair. Yak hair is commonly used in industry for testing hair-coloring compositions because it is pure white, virgin, and clearly shows differences between coloring formulations without background influences. The hair coloring compositions (juice) were applied to the hair swatches and allowed to process for 20 minutes (i.e., the coloring composition was allowed to remain on the hair at room temperature for 20 minutes). After 20 minutes, the hair swatches were rinsed with water while passing fingers through the hair (10 passes).

The hair swatches then were evaluated using the CIE L* a* b* system using a Minolta Spectrophotometer CM3600D colorimeter. In the L* a* b* system, the three parameters simply denote, respectively, the color intensity (L*), the green/red color axis (a*) and the blue/yellow color axis (b*). The L*a*b* colorimetric system is a colorimetric system that assigns each color to a position in a spherical color space. The brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively.

A lower L* represents a darker color (greater intensity).

The difference in overall coloring between colored hair swatches is defined by ($\Delta E^*$) according to the following equation:

$$\Delta E^* = \sqrt{(L^* - L_o^*)^2 + (a^* - a_o^*)^2 + (b^* - b_o^*)^2}$$

In this equation, $L^*$, $a^*$ and $b^*$ represent the values measured on colored (treated) hair swatches and $L_o^*$, $a_o^*$ and $b_o^*$ represent the values measured on uncolored (untreated) hair swatches or hair swatches treated with a different composition. This allow for quantification of differences in color (color uptake or color retention) between untreated versus treated hair swatches or between different samples of treated hair swatches. Typically, a $\Delta E^*$ value (or simply $\Delta E$) of 2 or greater between two samples is noticeable with the naked eye (human). The results are presented in the table below.

| | Red | | |
|---|---|---|---|
| | C (25% EtOH) | D (37.5% EtOH) | E (50% EtOH) |
| $\Delta L^*_{Yak} = L^*_{(Yak)} - L^*_{((C), (D), or (E))}$ | 49.4 | 47.6 | 45.6 |
| $\Delta L^*_{comparative} = L^*_{(C)} - L^*_{((D) or (E))}$ | Baseline | 1.8 | 3.8 |
| $\Delta E^* = E^*_{(C)} - E^*_{((D) or (E))}$ | Baseline | 2.5 | 3.9 |

| | Magenta | | |
|---|---|---|---|
| | F (25% EtOH) | G (37.5% EtOH) | H (50% EtOH) |
| $\Delta L^*_{Yak} = L^*_{(Yak)} - L^*_{((C), (D), or (E))}$ | 56.9 | 53.7 | 48.4 |
| $\Delta L^*_{comparative} = L^*_{(C)} - L^*_{((D) or (E))}$ | Baseline | 3.3 | 8.6 |
| $\Delta E^* = E^*_{(C)} - E^*_{((D) or (E))}$ | Baseline | 6.1 | 14.3 |

The data show that the color intensity ($\Delta L^*$) and overall color uptake ($\Delta E^*$) was significantly better for Compositions C and F, which had the lowest amount of ethanol (25 wt. %) and the highest amount of water (about 70 wt. %). As the amount of ethanol increased (and the amount of water decreased) the color intensity and overall color uptake worsened. Thus, the data show that replacing ethanol with water (to decrease the amount of ethanol and increase the amount of water) surprisingly improves color intensity and overall color uptake of direct dyes.

Example 3

(Comparative Testing - Tenacity)

| | INCI US | I (wt. %) Red | C-I (wt. %) Red | J (wt. %) Magenta | C-J (wt. %) Magenta |
|---|---|---|---|---|---|
| Direct Dye | BASIC YELLOW 87 & BASIC RED 51 | <1 | <1 | | |
| | BASIC RED 51 & HYDROXYANTHRAQUINONE-AMINOPROPYL METHYL MORPHOLINIUM METHOSULFATE | | | <1 | <1 |

(Comparative Testing - Tenacity)

| | INCI US | I (wt. %) Red | C-I (wt. %) Red | J (wt. %) Magenta | C-J (wt. %) Magenta |
|---|---|---|---|---|---|
| Nonionic Film Former | VP/VA COPOLYMER | 3 | | 3 | |
| Thickening Agent | HYDROXYETHYLCELLULOSE (nonionic) | 0.5 | 0.2 | 0.5 | 0.2 |
| | GUAR HYDROXYPROPYL-TRIMONIUM CHLORIDE (cationic) | | 0.1 | | 0.1 |
| Ethanol | ALCOHOL DENAT. | 25 | | 25 | |
| Water | WATER | 70.2 | 90.1 | 70.5 | 90.5 |
| Silicones | DIMETHICONE, BIS-PEG/PPG-14/14 DIMETHICONE, AND/OR AMODIMETHICONE | 0.8 | 1.1 | 0.8 | 1.1 |
| Water-Soluble Solvent | ISOPROPYL ALCOHOL | | 0.5 | | 0.5 |
| Cationic Surfactant | CETRIMONIUM CHLORIDE & BEHENTRIMONIUM CHLORIDE | | 2.1 | | 2.1 |
| Nonionic Surfactant | TRIDECETH-6 | | 0.1 | | 0.1 |
| Fatty Alcohol | CETYL ALCOHOL & CETEARYL ALCOHOL | | 4.8 | | 4.8 |
| Conditioning Agent | 2-OLEAMIDO-1,3-OCTADECANEDIOL | | 0.01 | | 0.01 |
| Filler | XYLOSE | 0.02 | | 0.02 | |
| Miscellaneous | SALTS, PH ADJUSTERS, BUFFERING AGENT, PRESERVATIVES, ETC. | ≤3 | ≤3 | ≤3 | ≤3 |

Testing was carried out to investigate the tenacity (long-term durability/hold) of the hair coloring compositions in the table above. Compositions I and J are inventive compositions (juice) that can be combined with propellant to create aerosol hair-coloring products. Compositions C-I and C-J are commercial benchmark products that are sold as direct dye creams. Testing was carried to investigate the tenacity of the inventive hair coloring compositions (juice) in comparison to the tenacity of the commercial benchmark direct dye creams. To ensure that any coloring differences between Inventive compositions I and J and the commercial benchmark compositions C-I and C-J is not due to different types and amounts of direct dyes, the same types and amounts of direct dyes were included in both. Compositions I and C-I include both basic yellow-87 and basic red-51 in the same amount. Compositions J and C-J include both basic red-51 and hydroxyanthraquinoneaminopropyl methyl morpholinium methosulfate in the same amount.

About 5 grams of each hair coloring composition from the table above was applied to swatches of yak hair. The hair coloring compositions were applied to the hair swatches and allowed to process for 20 minutes (i.e., the coloring compositions were allowed to remain on the hair at room temperature for 20 minutes). After 20 minutes, the hair swatches were rinsed with water while passing fingers through the hair swatches (10 passes). After rinsing, the hair swatches were shampooed 6 times using 0.4 g of shampoo per 1 gram of Yak hair.

After shampooing 6 times, the hair swatches were evaluated using the CIE L* a* b* system described above in Example 2. The results are presented in the tables below.

| | Red | |
|---|---|---|
| | I | C-I |
| $\Delta L^*_{comparative} = L^*_{(0)} - L^*_{(6\ washes)}$ | 1.2 | 1 |
| $\Delta E^* = E^*_{(o)} - E^*_{(6\ washes)}$ | 1.3 | 1.1 |

| | Magenta | |
|---|---|---|
| | J | C-J |
| $\Delta L^*_{comparative} = L^*_{(0)} - L^*_{(6\ washes)}$ | 2.6 | 2.5 |
| $\Delta E^* = E^*_{(o)} - E^*_{(6\ washes)}$ | 3.9 | 3.5 |

The data show that Inventive Compositions I and J exhibited similar tenacity to the commercial benchmark compositions C-I and C-J. Compositions I and J exhibited long lasting tenacity with reductions in color intensity ($\Delta L^*$) and overall color uptake ($\Delta E^*$) similar to that exhibited by the commercial benchmark compositions.

The terms "comprising," "having," and "including" are used in their open, non-limiting sense.

The terms "a" and "the" encompass the plural as well as the singular.

The compositions and methods of the present disclosure can comprise, consist of, or consist essentially of the essential elements and limitations set forth in the instant disclosure, as well as any additional or optional ingredients, components, or limitations described herein or that are otherwise useful.

All percentages, parts and ratios set forth herein are based upon the total weight of the compositions, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions may be modified in all instances, especially in the claims, by the term "about," meaning within +/−5% of the indicated number.

As used herein, the expression "at least one" is interchangeable with the expression "one or more" and thus includes individual components as well as mixtures/combinations.

The term "treat" (and its grammatical variations) as used herein refers to the application of the compositions of the present disclosure onto the surface of hair. The term 'treat" (and its grammatical variations) as used herein also refers to contacting hair with the hair treatment compositions of the present disclosure.

The compositions described throughout this disclosure may be a "rinse-off" product. A "rinse-off" product refers to a composition such as a hair treatment composition that is rinsed and/or washed with water either after or during the application of the composition onto the hair, and before drying and/or styling the hair. At least a portion of the composition is removed from the keratinous substrate during the rinsing and/or washing process.

The compositions described throughout this disclosure may be a "leave-on" product. A "leave-on" (also called leave-in) product refers to a hair treatment composition that is applied to hair and is not subjected to immediate rinsing and/or washing for at least 4 hours or for a period of time ranging from 4 hours up to 72 hours, from 4 hours up to 48 hours, or from 8 hours up to 36 hours, or from 8 hours up to 24 hours. In other words, the product is applied to the hair and remains on the hair, as styled.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, less than about 0.01 wt. %, or none of the specified material.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The cosmetically acceptable counter-ions mentioned throughout the disclosure may include, for example, an alkali metal, alkaline earth metal, methylsulfate, or ammonium counter-ion. This list of counter-ions, however, is non-limiting.

The expression "inclusive" for a range of concentrations means that the limits of the range are included in the defined interval.

"Volatile", as used herein, means having a flash point of less than about 100° C.

"Non-volatile", as used herein, means having a flash point of greater than about 100° C.

"Non-oxidative" means that the hair-coloring composition (or juice or product) does not require oxidizing agents (such as, for example, hydrogen peroxide) to chemically change the color of the hair. A hair-coloring composition (or juice or product) that is "free of oxidizing agents that alter the color of hair" may include substances that have the ability to oxidize other substances, but the aqueous coloring compositions do not rely on this mode of action to achieve the desired coloring of the hair. In other words, the hair-coloring composition (or juice or product) is not considered an oxidative the hair-coloring composition (or juice or product) as understood by those in the art.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions of the instant disclosure can optionally be free or essentially free of all components, elements, and steps positively recited throughout the instant disclosure.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Some of the various categories of components identified may overlap. In such cases where overlap may exist and the composition includes both components (or the composition includes more than two components that overlap), an overlapping component does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or only the fatty compound (the single fatty acid does not serve as both the nonionic surfactant and the fatty compound).

All publications, patent applications, and journal articles cited in this specification are herein incorporated by reference, and for any and all purposes, as if each individual publication were specifically and individually indicated to be incorporated by reference. In the event of an inconsistency between the present disclosure and any publications incorporated herein by reference, the present disclosure controls.

The invention claimed is:

1. An aerosol hair-coloring product comprising a canister, the canister comprising:
   a vapor phase comprising a propellant; and
   a hair coloring juice phase comprising:
   (a) about 0.01 to about 15 wt. %, based on the total weight of the juice phase, of at least one direct dye selected from nitro-phenylenediamines, nitro-aminophenols, azo dyes, anthraquinones, triarylmethane dyes, indophenols, and a mixture thereof;
   (b) about 0.1 to about 25 wt. %, based on the total weight of the juice phase, of at least one nonionic film forming polymer;
   (c) about 0.1 to about 10 wt. %, based on the total weight of the juice phase, of at least one thickening agent;
   (d) at least 40 wt. % of water, based on the total weight of the juice phase; and
   (e) 40 wt. % or less of ethanol, based on the total weight of the juice phase;
   wherein the weight ratio of water to ethanol (water:ethanol) is about 1:1 to about 5:1; and wherein the juice phase comprises volatile organic compounds (VOC) in an amount of less than 55 wt. %, based on the total weight of the juice phase.

2. The aerosol hair-coloring product of claim 1, wherein the total amount of volatile organic compounds (VOC) is less than 35 wt. %, based on the total weight of the juice phase.

3. The aerosol hair-coloring product of claim 1, wherein the at least one nonionic film forming polymer is selected from:
   polyalkyloxazolines;
   vinyl acetate homopolymers;
   vinyl acetate copolymers;
   homopolymers and copolymers of acrylic esters;
   copolymers of acrylonitrile and a nonionic monomer;
   styrene homopolymers;
   styrene copolymers;
   polyamides;
   vinylpyrrolidone homopolymers;
   copolymer of vinylpyrrolidone and vinyl acetate monomers;
   vinyllactam homopolymers including and polyvinylcaprolactam; and
   vinyllactam copolymers;
   poly(vinylpyrrolidone/vinyl acetate/vinyl propionate) terpolymers; and a mixture thereof.

4. The aerosol hair-coloring product of claim 1, wherein the at least one nonionic film forming polymer is selected from VP/VA copolymer (or PVP/VA copolymer), PVP, or a mixture thereof.

5. The aerosol hair-coloring product of claim 1, wherein the thickening agent is a nonionic thickening agent selected from polysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof.

6. The aerosol hair-coloring product of claim 1, wherein the thickening agent is an anionic thickening agent selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof.

7. The aerosol hair-coloring product of claim 6 comprising polyacrylate-3.

8. The aerosol hair-coloring product of claim 1 comprising about 50 to about 75 wt. % of water, based on the total weight of the juice phase.

9. The aerosol hair-coloring product of claim 1 comprising about 10 to about 30 wt. % of ethanol, based on the total weight of the juice phase.

10. The aerosol hair-coloring product of claim 1, wherein the ratio of water to ethanol (water:ethanol) is about 2:1 to about 4:1.

11. The aerosol hair-coloring product of claim 1, wherein the propellant is selected from the group consisting of dimethyl ether, propane, n-butane, isobutene, and a mixture thereof.

12. The aerosol hair-coloring product of claim 1 that is free of silicon powder, mica, titanium dioxide, iron oxide, bismuth oxychloride, diatomaceous earth, and aluminum-clad epoxy resin.

13. An aerosol hair-coloring product comprising a canister, the canister comprising:
    a vapor phase comprising a propellant; and
    a hair coloring juice phase comprising:
    (a) about 0.01 to about 15 wt. %, based on the total weight of the juice phase, of at least one direct dye selected from nitro-phenylenediamines, nitro-aminophenols, azo dyes, anthraquinones, triarylmethane dyes, indophenols, and a mixture thereof;
    (b) about 0.1 to about 25 wt. %, based on the total weight of the juice phase, of at least one nonionic film forming polymer selected from VP/VA copolymer (or PVP/VA copolymer), PVP, or a mixture thereof;
    (c) about 0.1 to about 10 wt. %, based on the total weight of the juice phase, of at least one anionic thickening agent selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof;
    (d) at least 50 wt. % of water, based on the total weight of the juice phase; and
    (e) 30 wt. % or less of ethanol, based on the total weight of the juice phase;
    wherein the weight ratio of water to ethanol (water:ethanol) is about 2:1 to about 4:1; and wherein the juice phase comprises volatile organic compounds (VOC) in an amount of less than 35 wt. %, based on the total weight of the juice phase.

14. A hair coloring composition comprising:
    (a) about 0.01 to about 15 wt. % of at least one direct dye selected from nitro-phenylenediamines, nitro-aminophenols, azo dyes, anthraquinones, triarylmethane dyes, indophenols, and a mixture thereof;
    (b) about 0.1 to about 25 wt. % of at least one nonionic film forming polymer;
    (c) about 0.1 to about 10 wt. % of at least one thickening agent;
    (d) at least 40 wt. % of water; and
    (e) 40 wt. % or less of ethanol;
    wherein the weight ratio of water to ethanol (water:ethanol) is about 1:1 to about 5:1;

wherein the hair coloring composition comprises volatile organic compounds (VOC) in an amount of less than 55 wt. %; and all percentages by weight are based on the total weight of the hair coloring composition.

15. The hair coloring composition of claim 14, wherein the at least one nonionic film forming polymer is selected from:
polyalkyloxazolines;
vinyl acetate homopolymers;
vinyl acetate copolymers;
homopolymers and copolymers of acrylic esters;
copolymers of acrylonitrile and a nonionic monomer;
styrene homopolymers;
styrene copolymers;
polyamides;
vinylpyrrolidone homopolymers;
copolymer of vinylpyrrolidone and vinyl acetate monomers;
vinyllactam homopolymers including and polyvinylcaprolactam; and
vinyllactam copolymers;
poly(vinylpyrrolidone/vinyl acetate/vinyl propionate) terpolymers; and a mixture thereof.

16. The hair coloring composition of claim 14, wherein the at least one nonionic film forming polymer is selected from VP/VA copolymer (or PVP/VA copolymer), PVP, or a mixture thereof.

17. The hair coloring composition of claim 14, wherein the thickening agent is a nonionic thickening agent selected from olysaccharides, modified or unmodified starches, amylose, amylopectin, glycogen, dextrans, celluloses, cellulose derivatives, xylans, glucans, arabans, galactans, chitin, agars, locust bean gums, mannans, and a mixture thereof.

18. The hair coloring composition of claim 14, wherein the thickening agent is an anionic thickening agent selected from polyacrylate-3, carbomers, acrylates/C10-30 alkyl acrylate crosspolymers, acrylates/C10-30 alkyl acrylate crosspolymer, AMP-acrylates/allyl methacrylate copolymer, polyacrylate crosspolymer-6, a crosslinked methacrylic acid/ethyl acrylate copolymer (acrylates copolymer), and a mixture thereof.

19. A method for coloring hair comprising:
(i) applying the hair coloring composition of claim 14 onto hair;
(ii) allowing the hair coloring composition to remain on the hair for about 5 to about 30 minutes; and
(iii) rinsing the hair coloring composition from the hair.

20. A method for coloring hair comprising:
(i) spraying the hair coloring juice phase from the hair coloring product of claim 1 onto hair;
(ii) allowing the hair coloring juice phase to remain on the hair for about 5 to about 30 minutes; and
(iii) rinsing the hair coloring juice phase from the hair.

* * * * *